United States Patent
Mukherjee et al.

(10) Patent No.: US 6,783,963 B2
(45) Date of Patent: Aug. 31, 2004

(54) PROCESS FOR THE PREPARATION OF METAL SULFIDE NANOPARTICLES

(75) Inventors: Priyabrata Mukherjee, Pune (IN); Deendayal Mandal, Pune (IN); Absar Ahmad, Pune (IN); Murali Sastry, Pune (IN); Rajiv Kumar, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/108,927

(22) Filed: Mar. 29, 2002

(65) Prior Publication Data

US 2003/0186404 A1 Oct. 2, 2003

(51) Int. Cl.$^7$ .............................. C12P 3/00; C12P 1/02
(52) U.S. Cl. ...................................... 435/168; 435/171
(58) Field of Search ............................. 43/41; 435/41, 435/168, 171

(56) References Cited

U.S. PATENT DOCUMENTS 6,537,344 B2 * 3/2003 Mukherjee et al. ........... 75/362

OTHER PUBLICATIONS

Kreger–van Rij. The Yeasts a Taxonomic study. 1984, Elsevier Science Publishers B.V., Armsterdam, p. 1.*
Srivastava et al. Biotechnology and Bioengineering Symposium, 1985, vol. 15, pp. 491–499.*
Dameron et al., Nature, 1989, 338–339.*

* cited by examiner

*Primary Examiner*—Christopher R. Tate
*Assistant Examiner*—Kailash C. Srivastava
(74) *Attorney, Agent, or Firm*—Sughrue Mion, PLLC

(57) ABSTRACT

The process of the invention reports a new biological method, instead of chemical or physical methods, for preparing colloidal nano-sized metal sulphides using fungi.

12 Claims, No Drawings

PROCESS FOR THE PREPARATION OF METAL SULFIDE NANOPARTICLES

FIELD OF THE INVENTION

The present invention relates to a process for the preparation of metal sulfide nanoparticles. More particularly, it relates to the said new process employing an efficient, easy and environmentally friendly method for preparing stable, colloidal metal sulfide nano-particles in aqueous solutions using naturally occurring bio-materials such as fungi.

BACKGROUND OF THE INVENTION

Nano-particles are extremely important materials in different areas ranging from nano-technology, non-linear optics, diode lasers, smart sensors, markers in drugs, gene sequencing to catalysis. Nano-materials can be obtained by various chemical and physical methods. Some examples of physical methods are vapor deposition, lithographic processes and molecular beam epitaxy (MBE) of metal sulphides such as cadmium sulfide, (CdS), lead sulphide (PbS), zinc sulphide (ZnS), silver sulphide ($Ag_2S$), molybdenum sulphide ($MoS_2$) etc. Chemical methods for the preparation of metal sulphide nanoparticles are based on the reaction of metal ions in solution either with $H_2S$ gas or $Na_2S$ in aqueous medium (V. L. Colvin, A. N. Goldsmith and A. N. Alivisatos, *J. Am. Chem Soc.* 1992, 114, 5221). In order to stabilize the particles in solution, capping of the particles with thiol derivatives is resorted to. It may be pertinent to mention that yeast has also been used for the preparation of CdS nanoparticles (C. T. Dameron, R. N. Reese, R. K. Mehra, A. R. Kortan, P. J. Carroll, M. L. Steigerwals, L. E. Brus and D. R. Winge, Nature 1989, 338, 596), where the sulphur source is provided by naturally occurring glutathiones present in the yeast. However, this method involves the formation of CdS nanocrystallites inside the cell and extraction of the CdS from the cell is very complex.

The methods mentioned above suffer from drawbacks such as being environmentally hazardous (chemical methods using $H_2S$ etc.) and resulting in the quick agglomeration of nano-particles leading to big particles of poor mono dispersity. Although specific capping agents are used in some of the above mentioned methods to restrict the size of the colloidal metal particles and to stabilize the particle size distribution, this makes the whole system multi-step complicated and user unfriendly.

In the view of the above drawbacks of prior art methods, it was necessary to develop a new method overcoming those drawbacks.

OBJECTS OF THE INVENTION

The main object of the present invention of provide a new process for the preparation of nano particles of metals naturally occurring fungi under aqueous medium.

Another object is to provide an environmentally friendly process using biological methods avoiding use of hazardous chemicals.

SUMMARY OF THE INVENTION

The process used in the present invention reports a new biological method, instead of chemical or physical methods, for preparing colloidal nano-sized metal sulphides. This is for the first time when fungi are used to efficiently prepare colloidal CdS nano-particles from the aqueous solution of cadmium sulphate.

Accordingly, the present invention provides a new process for the preparation of metal sulphide nano particles, which comprises treating wet fungus or fungus extract with a metal sulphate solution at temperature ranging between 15 to 40° C. for a period ranging between 2 to 120 hrs., separating the biomass by conventional methods to obtain the corresponding colloidal metal sulphide nano particles.

In one embodiment of the invention, the metal sulphate is selected from the group consisting of cadium sulphate, lead sulphate, zinc sulphate, nickel sulphate, molybdenum sulphate and silver sulphate.

In another embodiment the wet fungus is obtained by growing the *Fusarium oxysporum* sp. in a conventional culture medium for a period of 2 or more hours at temperature ranging between 15–40° C. under aseptic conditions, separating the biomass by conventional methods like centrifugation, washing several times with sterile water, and then incubating the whole reaction mixture at 15 to 40° C. and atmospheric pressure.

In another embodiment the fungus extract is obtained by treating the wet fungus with water under aseptic conditions at temperature ranging 15 to 40° C. for 2 or more hours.

In yet another embodiment the metal sulphate source is a combination of cadmium ions and a source of sulphur.

In yet another embodiment the source of cadmium ions is a water soluble cadmium salt selected from the group consisting of nitrates, halides and carbonate.

In yet another embodiment, the source of sulphur selected from the group consisting of metal sulphates, sulphites or sulphides exemplified by sodium sulphate, sodium sulphite, sodium sulphide and hydrogen sulphide.

In another embodiment the metal sulphate solution is obtained by dissolving the corresponding metal sulphate in water.

In yet another embodiment of the present invention the concentration of the metal sulphate per gram of the wet fungus or fungus is in the range of 10 to 200 mg. preferably 10–100 mg metal sulphate per gram of the wet fungus extract, and most preferably in the range of 25–100 mg metal sulphate per gram of the wet fungus or fungus extract.

In yet another embodiment the weight ratio of water to the wet fungus or fungus extract is in the range of 1 to 100.

In one embodiment of the invention the fungus is chosen from different species of *Fusarium oxysporum*, taken as whole cell as wet solid mass or fungus extract.

In another feature of the invention, the reaction of the fungus and a source of metal sulphate in solution is preferably be carried out in water.

In yet another feature of the invention the incubation/reaction temperature is in the range of 15–40° C. the preferred range is 23–33° C. However, the most preferred range of the incubation/reaction temperature is 25–29° C.

DETAILED DESCRIPTION OF THE INVENTION

The process for the present invention may be described here with examples that are illustrative only and should not be construed to limit the scope of the present invention.

EXAMPLE 1

In this experiment, 10 g of the wet fungus (*Fusarium oxysporum*), which was grown in a culture medium, separated from the medium by centrifugation, washed several times with sterile water through centrifugation, was taken in an autoclaved conical flask and then 100 ml solution of 100 mg of cadmium sulphate, herein after denoted as $CdSO_4$, in water was added and the conical flask was then plugged with cotton and incubated at 27° C. The samples were collected from time to time by filtration of the solution containing the fungus inside the inoculation chamber under laminar flow condition. The samples were collected at different time between 2 and 120 hours and each sample was characterized by transmission electron microscopy, herein after denoted as TEM and x-ray diffraction, herein after denoted as XRD, for size determination and phase identification. The cadmium sulphide particles obtained were in the range of 2–10 nano meters.

EXAMPLE 2

In this experiment, 10 g of the wet fungus (*Fusarium oxysporum*), growth in a culture medium, separated from the medium by centrifugation, washed several times with water through centrifugation, was taken in an autoclaved conical flask and then a solution containing 25 mg of $CdSO_4$ in 100 ml water was added, and the conical flask was then plugged with cotton and incubated at 27° C. The samples were collected from time to time by filtration of the solution containing the fungus inside the inoculation chamber under laminar flow condition. The samples were collected at different time intervals between 2–72 hours and each stage was by TEM and XRD. The CdS particles were in the range of 3–8 nm.

EXAMPLE 3

In this experiment, 10 g of the wet fungus (*Fusarium oxysporum*), grown in a culture medium, separated from the medium by centrifugation, washed several times with water through centrifugation, was taken in an autoclaved conical flask and then 250 mg of $CdSO_4$ in 100 ml water were added and the conical flask which was then plugged with cotton and incubated at 27° C. The samples were collected from time to time by filtration of the solution containing the fungus inside the inculation chamber under laminar flow condition. The samples were collected between 2–120 h and each stage was characterized by TEM and XRD where the particle size of CdS nano-particles was found to be in the range 2–10 nm.

EXAMPLE 4

In this experiment the 10 g of the wet fungus (*Fusarium oxysporum*), grown in a culture medium, seprated from the medium by centrifugation, washed several times with water through centrifugation, was first inoculated at 27° C. for 12 h, filtered out and to the 100 g clear that fungus extract, taken a conical flask, 100 mg of $CdSO_4$ were added and kept at 27C. The samples were collected from time to time by filtration of the solution containing the fungus extract inside the inoculation chamber under laminar flow condition. The samples were collected between 2–120 h and each stage was characterized by TEM and XRD where the particle size was in the range 2–7 nm.

EXAMPLE 5

In this experiment, 10 g of the wet fungus (*Fusarium oxysporum*), which was grown in a culture medium, separated from the medium by centrifugation, washed several times with water through centrifugation, was taken in an autoclaved conical flask and then 100 ml solution of 100 mg of zinc sulphate ($ZnSO_4$) in water were added and the conical flask was the plugged with cotton and incubated at 27° C. The samples were collected at 4, 24, 60 and 120 hours by filtration of the solution containing the fungus inside the inoculation chamber under laminar flow condition and each sample was characterized by Tem and XRD diffraction where the size of colloidal nano-particles was in the range of 4–8 nm.

EXAMPLE 6

In this experiment, 10 g of the wet fungus (*Fusarium oxysporum*), grown in a culture medium, separated from the medium by centrifugation, washed several times with water through centrifugation, was taken in an autoclaved conical flask and then a solution containing 25 mg of lead sulphate ($PbSO_4$) in 100 ml water was added, and the conical flask was then plugged with cotton and incubated at 27° C. The samples were collected from time to time between 2–72 hours by filtration of the solution containing the fungus inside the inoculation chamber under laminar flow condition and the colloidal PbS particles were characterized by TEM and XRD where particle size is found to be in the range of 2–10 nm.

EXAMPLE 7

In this experiment, 10 g of the wet fungus (*Fusarium oxysporum*), grown in a culture medium, separated from the medium by centrifugation, washed several times with water through centrifugation, was taken in an autoclaved conical flask and then 250 mg of molybdenum sulphate in 100 ml water added and the conical flask which was then plugged with cotton and incubated at 27° C. The samples were collected from time to time between 2–120 h by filtration of the solution containing the fungus inside the inoculation chamber under laminar flow conditon and colloidal molybdenum sulphine ($MoS_2$) samples were characterized by XRD and TEM where the particles size is found to be in the range 2–10 nm.

EXAMPLE 8

In this experiment the 10 g of the wet fungus (*Fusarium oxysporum*), grown in a culture medium, separated from the medium by centrifugation, washed several times with water through centrifugation, was taken in an autoclaved conical flask and then a solution of 100 mg of silver sulphate ($Ag_2SO_4$) in 100 ml water was added and kept at 27° C. The samples were collected from time to time between 2–120 h by filtration of the solution containing the fungus extract inside the inoculation chamber under laminar flow condition. The samples were collected and each stage was characterized by TEM where the particle size is found to be in the range 2–10 nm. Samples were further characterized by X-ray diffraction.

EXAMPLE 9

In this experiment, 10 g of the wet fungus (*Fusarium oxyspurm*), grown in a culture medium, separated from the medium by centrifugation, washed several times with water through centrifugation, was taken in an autoclaved conical flask and a solution of 100 mg of nickel sulphate ($NiSO_4$) in 100 ml water was added and kept at 27° C. The samples were collected from time to time between 2–120 h by filtration of the solution containing the fungus extract inside the inoculation chamber under laminar flow condition. The samples were collected and each stage was characterized by TEM where the particle size is found to be in the range 4–10 nm. The samples were further characterized by the X-ray diffraction.

EXAMPLE 10

This experiment shows use of external sulphate source other than metal sulphate where metal salt is other than the sulphate such chloride, nitrate carbonate etc. In this experiment the 10 g of the wet fungus (*Fusarium oxysporum*), grown in a culture medium, separated from the medium by centrifugation, washed several times with water through centrifugation, were taken in an autoclaved conical flask and then 100 ml solution containing 92 mg of cadmium chloride and 142 mg sodium sulphate ($Na_2SO_4$) was added and the whole mixture was incubated at 27° C. The samples were collected from time to time between 2–120 h by filtration of the solution containing the fungus extract inside the inoculation chamber under laminar flow condition. The samples were collected and each stage was characterized by TEM where the particle size is found to be in the range 3–10 nm. The samples were further characterized by the X-ray diffraction.

Major advantage of the present invention is the use of cadmium sulfate for the preparation of metal-suphide nano-articles where the fungi provides "sulphate reductase" which catalyzes the metal sulphate into metal sulphide without using any externally added reducing agent.

Another major feature of the present invention is that the colloidal nano-sized metal sulphides are quite stable in the aqueous solution. Further, the present method is quite simple and environmentally friendly.

Yet another advantageous feature of our present invention is that the reduction process is extra-cellular, where the formation of nano-particles is occurring in the solution and not inside the cell of fungus. This is a very important advantage of the present invention from the practical utility point of view, because of the ease of harnessing the colloidal metal sulphide nanoparticles by depositing on to appropriate solid films using conventional methods.

We claim:

1. A process for the preparation of metal sulphide nano size particles, which comprises contacting wet fungus with a metal sulphate aqueous solution at temperature ranging between 15 to 40° C. for a period ranging between 2 to 120 hrs to obtain a composition containing metal sulphide nano size particles, and separating the fungus from the metal sulphide nano size particles to thereby obtain the metal sulphide nano size particles.

2. A process as claimed in claim 1, wherein the metal sulphate is selected from the group consisting of cadium sulphate, lead sulphate, zinc sulphate, nickel sulphate, molybdenum sulphate and silver sulphate.

3. A process as claimed in claim 1, wherein the wet fungus is obtained by growing *Fusarium oxysporum* sp. in a culture medium for a period of 2 or more hours at temperature ranging between 15–40° C. under aseptic conditions to produce a biomass, separating the biomass by centrifugation, washing the separated biomass several times with sterile water, and then incubating the biomass and metal sulphate mixture at 15 to 40° C. and at atmospheric pressure.

4. A process for the preparation of metal sulphide nano size particles, which comprises contacting wet fungus with an aqueous solution containing a combination of cadmium ions and a source of sulphur at a temperature ranging between 15–40° for a period ranging between 2 to 120 hours to obtain a composition containing metal sulphide nano size particles, and separating the fungus from the metal sulphide nano size particles to thereby obtain the metal sulphide nano size particles.

5. A process as claimed in claim 4, wherein the cadmium ions are provided by a water soluble cadmium salt selected from nitrates, halides and carbonates.

6. A process as claimed in claim 4, wherein the source of sulphur is selected from the group consisting of sulphates, sulphur and sulphides.

7. A process as claimed in claim 5, wherein the source of sulphur is selected from the group consisting of sodium sulphate, sodium sulphite, sodium sulphide and hydrogen sulphide.

8. A process as claimed in claim 1, wherein the metal sulphate solution is obtained by dissolving a metal sulphate in water.

9. A process as claimed in claim 1, wherein the concentration of the metal sulphate per gram of the wet fungus is in the range of 10 to 200 mg.

10. A process as claimed in claim 1, wherein the fungus is selected from a species of Fusarium, taken as whole cell as wet solid mass.

11. A process as claimed in claim 9, wherein the concentration of the metal sulphate is 10–100 mg metal sulphate per gram of the wet fungus.

12. A process as claimed in claim 9, wherein the concentration of the metal sulphate is 25–100 mg metal sulphate per gram of the wet fungus.

* * * * *